US008666696B2

(12) United States Patent
Hanai

(10) Patent No.: US 8,666,696 B2
(45) Date of Patent: Mar. 4, 2014

(54) REED TESTING DEVICE FOR SINGLE-REED INSTRUMENT

(76) Inventor: Khoi Hanai, Tokyo (JP)

( * ) Notice: Subject to any disclaimer, the term of this patent is extended or adjusted under 35 U.S.C. 154(b) by 379 days.

(21) Appl. No.: 13/000,574

(22) PCT Filed: Jul. 5, 2010

(86) PCT No.: PCT/JP2010/004370
§ 371 (c)(1),
(2), (4) Date: Jan. 27, 2011

(87) PCT Pub. No.: WO2011/004574
PCT Pub. Date: Jan. 13, 2011

(65) Prior Publication Data
US 2011/0166822 A1  Jul. 7, 2011

(30) Foreign Application Priority Data
Jul. 9, 2009  (JP) .................................. 2009-162327

(51) Int. Cl.
*G01C 9/00* (2006.01)
*G01C 17/00* (2006.01)
*G01C 19/00* (2013.01)
*G10D 9/02* (2006.01)
*G01N 3/20* (2006.01)

(52) U.S. Cl.
CPC ....................................... *G01N 3/20* (2013.01)
USPC ........................................ 702/150; 84/383 A

(58) Field of Classification Search
CPC .. G01N 2033/0078; G01N 3/20; G10D 9/023
USPC ............... 702/150; 73/812, 849, 862.26, 651; 409/132, 133; 84/729, 732, 350, 363, 84/375, 383
See application file for complete search history.

(56) References Cited

U.S. PATENT DOCUMENTS 3,477,133 A * 11/1969 Armato ....................... 29/407.05
5,127,778 A *  7/1992 Scheer ........................... 409/132
6,683,238 B1   1/2004 Driscoll, Jr.

FOREIGN PATENT DOCUMENTS

JP  4001907   8/2007
JP  4022248  10/2007

OTHER PUBLICATIONS

Masuda, Hideyuki; "Cantilever Type Reed Stimulation for Saxophone based on the Finite Difference Method", Yamaha Corporation, Musical Acoustics, vol. 28, No. 1, May 30, 2009, pp. 45-50.
Mukhopadhyay, Subhas Chandra et al.; "Saxophone Reed Inspection Employing Planar Electromagnetic Sensors", IEEE Translations on Instrumentation and Measurement, vol. 56, No. 6, Dec. 27, 2007, pp. 2492-2503.

* cited by examiner

*Primary Examiner* — John Breene
*Assistant Examiner* — Manuel Rivera Vargas

(57) ABSTRACT

Objective index is indicated with respect to the characteristic comparison between the front and the back sides of the reed, the right and left balance, and the hardness characteristic compared to the reference reed. A holder guiding member 11 is disposed on a rotating table 2, and a holder 10 is detachably mounted on the holder guiding member 11. The holder 10 holds the test object reed R. Testing of the front and the back surfaces of the reed R is performed by turning the holder 10 upside down. A probe 20 is made contact with the surface of the reed R with the constant pressure force, and the deformation degree of the probe 20 is detected by a displacement sensor 30 with rotating the rotating table 2. The rigidity distribution of reed R in the width direction is obtained by the displacement sensor 30. The rigidity distribution characteristics of the front and the back sides are tested by displaying the front-side characteristic graph and the reversed back-side characteristic graph on one screen. The balance index is calculated from the areas resultantly generated by superimposing the front-and-back-side characteristic graphs with the reversed graphs thereof. The hardness index is obtained based on the integrating value of the front-and-back-side characteristics and the integrating value of the front-and-back-side characteristics of the reference reed.

9 Claims, 11 Drawing Sheets

REED TESTING DEVICE FOR SINGLE-REED INSTRUMENT

TECHNICAL FIELD

This invention relates to a testing device of a reed for a single-reed instrument.

BACKGROUND ART

For a woodwind reed musical instrument, the quality of the reed is an essential factor that decisively influences e.g. the timbre and the responsibility of the instrument, and also influences the quality of playing. Reeds for single-reed instruments, such as a clarinet family and a saxophone family, are commercially sold by various manufacturers, and most players use such commercially manufactured reeds. However, even if the reeds are manufactured in the same lot of the manufacturer, only a few of them have a quality usable in a concert with their original state, while most of them are dissatisfactory because, for example, they cause noise, have difficulty in controlling a sound freely from a small sound to a loud sound, provide only poor sound in spite of the breath blown into, provide an insufficient sound in a low-pitched sound region or in a high-pitched sound region, or have combined defects thereof.

Players manage to find out a better one among such reeds and use the reed, though not satisfactory. Some players make an adjustment to the reed based on their own experiences, however, such experiences are, like the playing skill of instruments, hardly made into documentation, and therefore a common concrete method available to everyone has not been known.

As an index for finding out a good sounding reed, it is slightly indicated to select e.g. a reed that has a grain (vascular bundle) running straight and has thickness varying smoothly from the center toward the vibrating tip.

Although most commercially manufactured reeds satisfy such criteria, various defects are found when placing the reed on the instrument and doing a test play. If a good sounding reed is found by chance, it is difficult to find out a significant visual difference between the good sounding reed and other dissatisfactory reeds. There is a method for drawing contour lines of the thickness distribution by measuring a number of points using e.g. a micrometer, however, this method cannot be readily performed.

Therefore, doing a test play by placing the reed on the instrument was only a method for determining the quality of the reed. Various methods have been proposed for adjusting a dissatisfactory reed to be satisfactory, however, most of the methods are unstable and lack objectivity since they depend on the individual feeling, and in most cases, more serious defects are generated in other points as a result of trying adjustment by those methods. Resultantly, most of the reeds have been discarded due to the failure.

As a method for solving the above problems, the applicant of the present application proposed "Testing device for inspecting rigidity distribution of a reed for a single-reed instrument" as disclosed in Patent document 1. This invention is characterized in comprising:

(1) a table for fastening a reed for a single-reed instrument in a state where a vibrating tip of the reed is suspended in the air;
(2) a probe for applying a force to the fastened reed in the vertical direction so as to detect the rigidity;
(3) a mechanism for moving a probe contacting point on the reed back-and-forth and right-to-left; and
(4) means for detecting the displacement of the probe contacting point.

The invention disclosed in Patent document 1 is based on the applicant's knowledge that the good sounding reed has the rigidity distribution characteristics of the vibrating tip region that is substantially symmetrical with respect to the central axis of the reed and has a gradual distribution. The testing device indicates whether the test object reed satisfies this condition or not, and when the reed dissatisfies the condition, further indicates which portion of the reed dissatisfies the condition.

According to the invention disclosed in Patent document 1, it becomes possible to test the quality of the reed without placing the reed on the instrument and doing a test play, which was inevitable in prior art. Furthermore, regarding the defective reed, hidden cause of the defects can be found out, and adjustment points necessary for improvement can be identified, therefore even the reeds conventionally discarded as unused can be improved to be usable in the public playing. In particular, an aspect of the rigidity distribution of the reed can be automatically detected and shown objectively, thereby achieving an advantage that it is possible for any one to determine the quality of the reed.

Patent document 1: Japanese Patent No. 4022248

DISCLOSURE OF THE INVENTION

The invention disclosed in Patent document 1 is innovative as a reed testing device, which has not been shown in prior art. However, the applicant has further tried to improve the invention according to Patent document 1 and thus achieved the following ideas.

(a) According to the invention disclosed in Patent document 1, the rigidity distribution characteristics are inspected only from the front side of the reed, though, is it possible to do the similar test also from the back side of the reed?
(b) It is preferable that the rigidity distribution characteristics of the reed maintain a balance between the right side and the left side of the reed. Is it possible to provide an objective index with respect to the balance as a test result?
(c) Is it possible to provide as a test result an objective index for indicating at which degree the rigidity (hardness) of the test object reed conforms to the reference reed?

The present invention is proposed based on the above ideas. That is, the object of the present invention is to provide a reed testing device for a single-reed instrument that solves the above technical problems (a)-(c).

To achieve the above object, a reed testing device for a single-reed instrument according to the present invention is characterized by a displacement sensor which detects the rigidity distribution characteristics of a reed with respect to both a front and a back surfaces of the reed; and displaying characteristic graphs of the front and the back surfaces created by said displacement sensor on one screen.

Furthermore, according to another aspect of the present invention, the characteristic graphs obtained with respect to the front and the back surfaces of the reed with the graphs obtained by reversing left and right of said characteristic graphs, differences between said created characteristic graphs and said reversed characteristic graphs are quantitatively determined, and an index regarding a right and left balance of the reed is outputted. Moreover, according to another aspect of the present invention, characteristics of a reference reed are compared with characteristics of a test object reed and a comparison result is displayed quantitatively.

According to the present invention, comparison between the respective characteristics of the front and the back surfaces of the reed, the right and left balance of the reed, and hardness characteristics of the reed compared with the reference reed can be indicated by means of objective indices. As a result, it becomes possible to adjust or select the reed more accurately.

EXPLANATION OF REFERENCE NUMERALS

Figure 1:
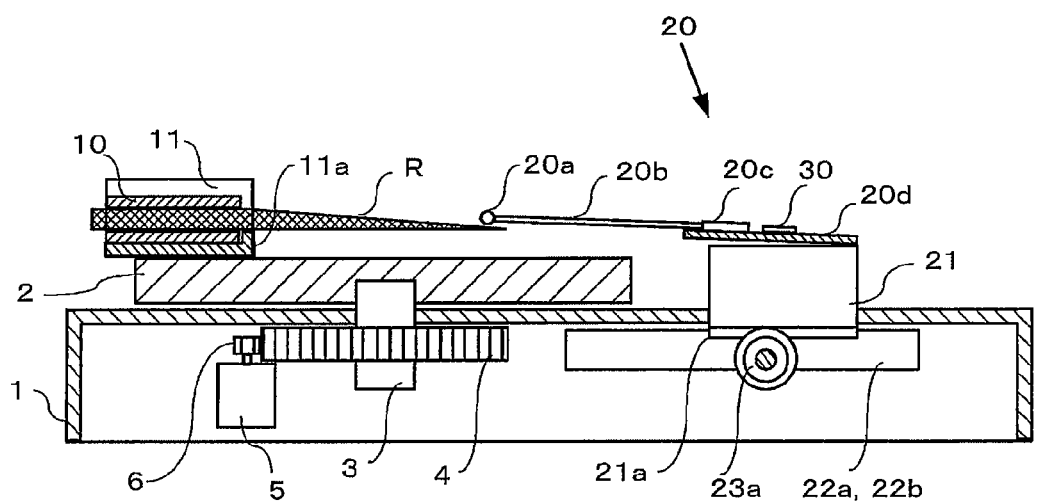
FIG. 1 is a side view showing a mechanism portion according to a first embodiment.

1 . . . Base
2 . . . Rotating table
2a . . . Scale board
3 . . . Rotation shaft
4 . . . Gear
5 . . . Potentiometer
6 . . . Gear
10 . . . Holder
11 . . . Holder guiding member
12 . . . Fastening member
13 . . . Holder bar
20 . . . Probe
21 . . . Supporting member
21a . . . Rack
22a, 22b . . . Rails
23 . . . Knob
23a . . . Pinion
30 . . . Displacement sensor
31 . . . Processing circuit
31a . . . Characteristic graph creation unit
31b . . . Characteristic graph storing unit
31c . . . Comparative calculation unit
32 . . . Display unit

BEST MODE FOR CARRYING OUT THE INVENTION (First Embodiment)

In the following, a first embodiment according to the present invention will be explained in detail with reference to the accompanied drawings.

(Structure of First Embodiment)

Figure 2:
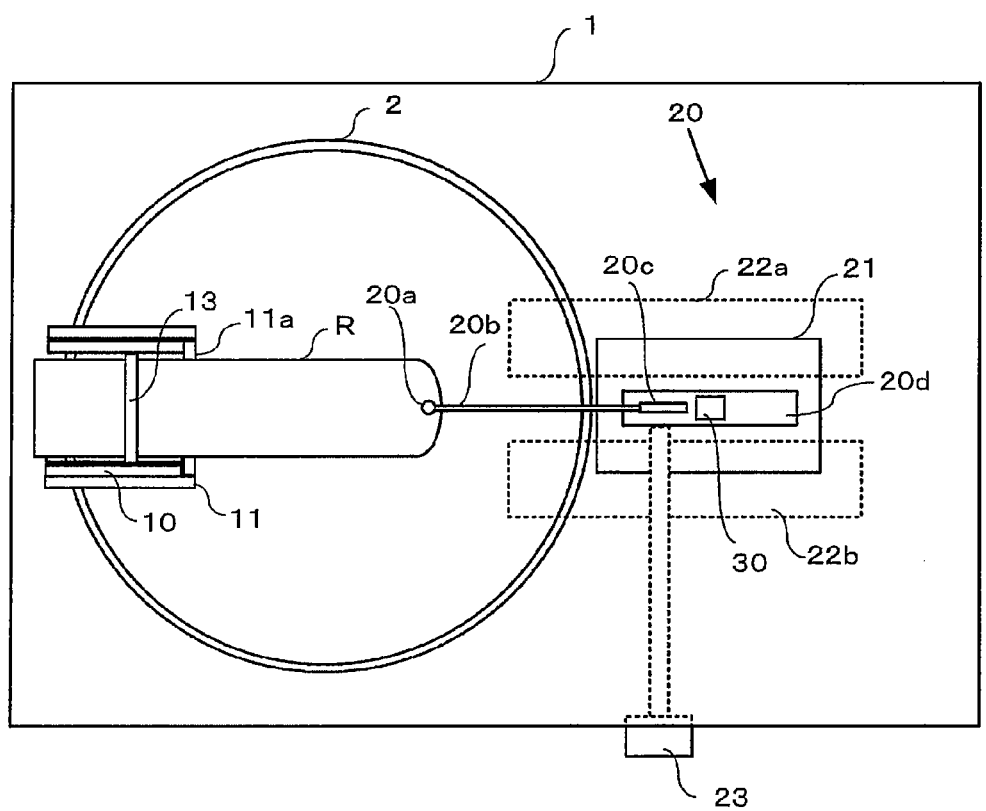
FIG. 2 is a plan view showing a mechanism portion according to the first embodiment.
Figure 3:
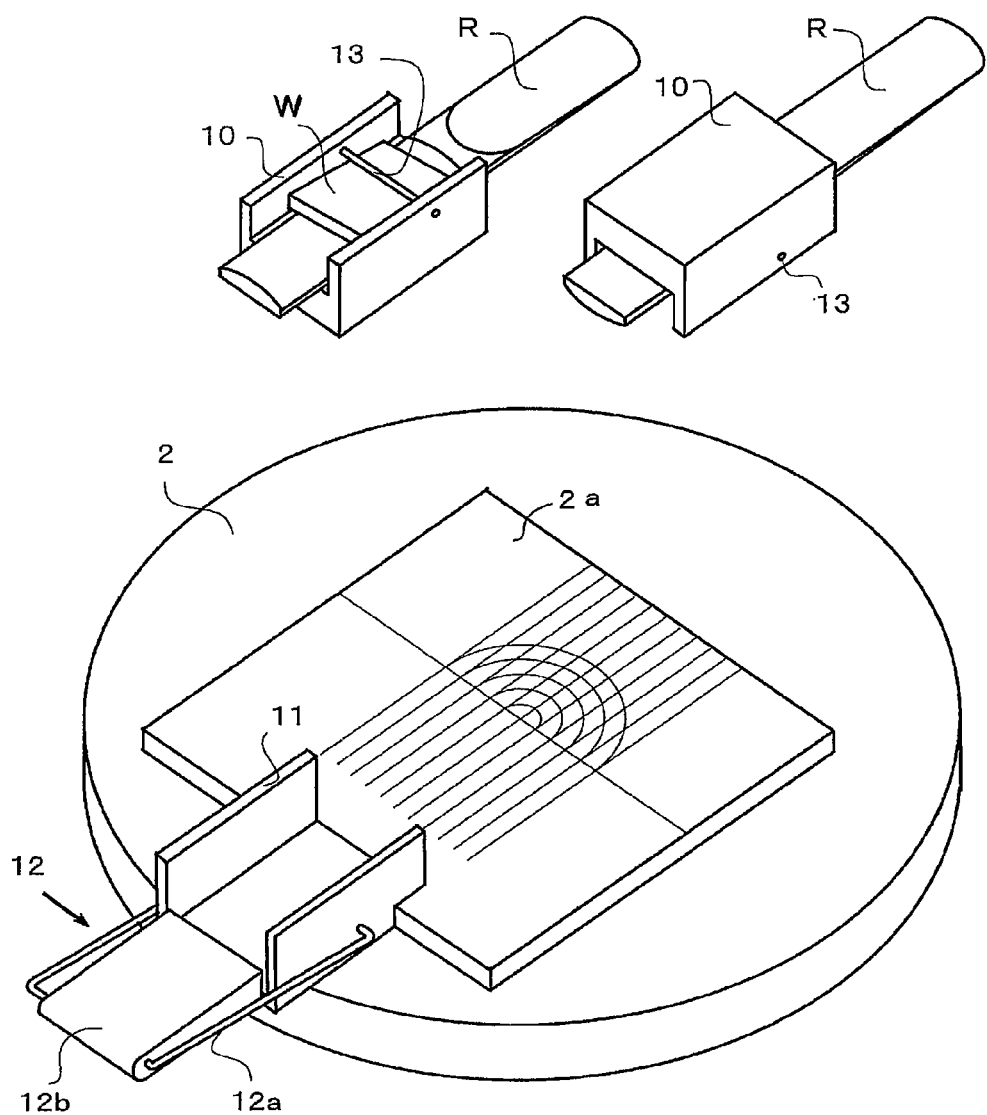
FIG. 3 is an enlarged perspective view showing a mechanism of a mounting portion of the reed according to the first embodiment.
Figure 4:
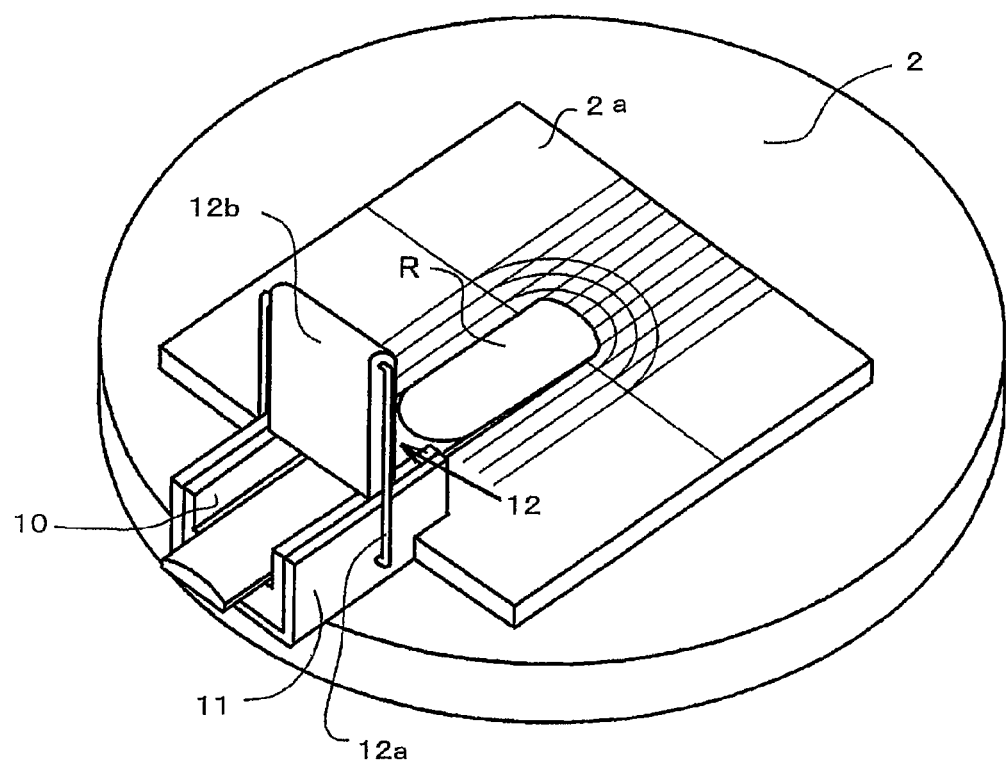
FIG. 4 is an enlarged perspective view showing a state where the reed is fixedly mounted according to the first embodiment.
Figure 5:
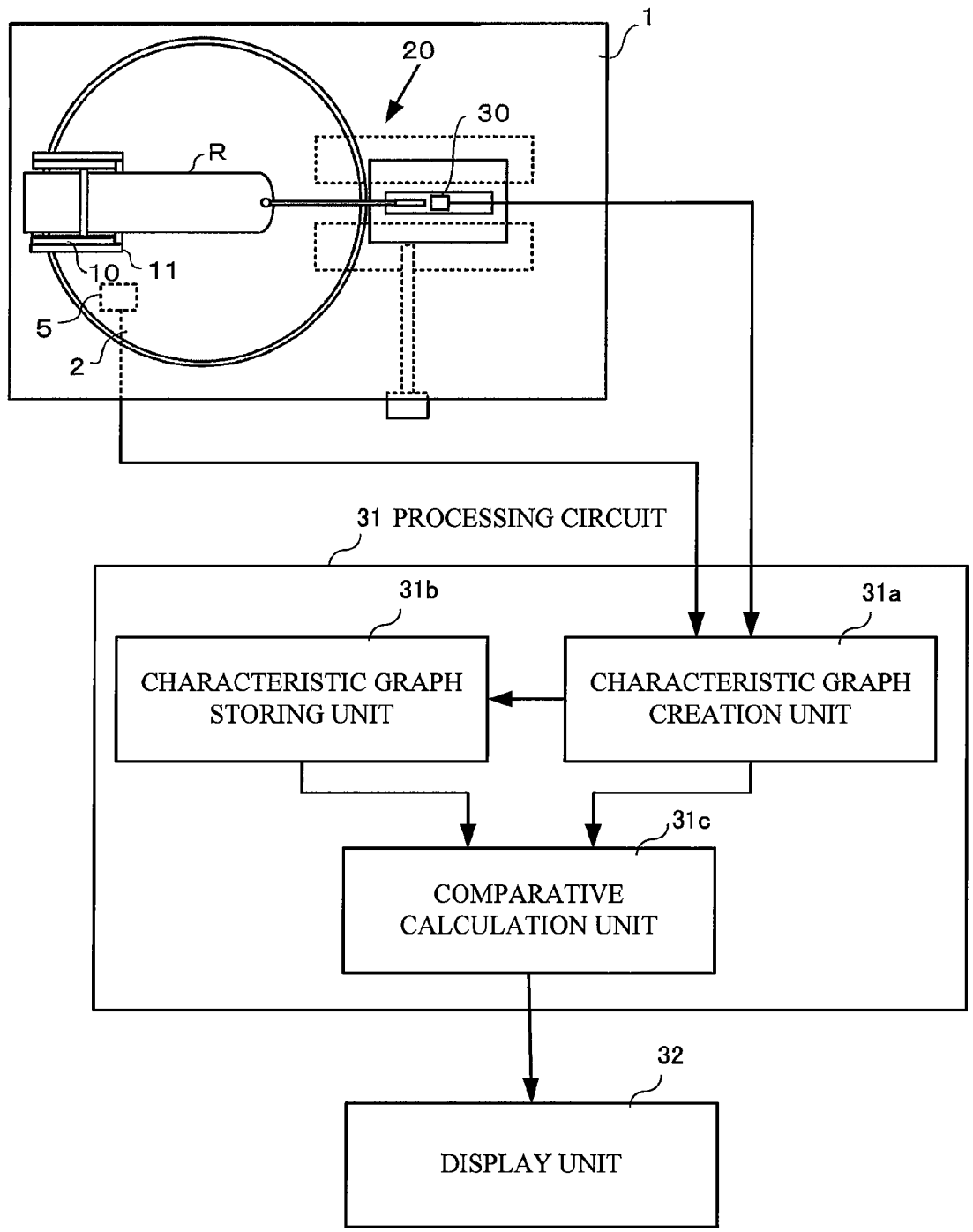
FIG. 5 is a wiring diagram showing a circuit portion according to the first embodiment.

FIG. 1 is a side view showing a mechanism portion according to the first embodiment, and FIG. 2 is a plan view thereof. FIG. 3 is an enlarged perspective view showing a mechanism of a mounting portion of the reed according to the first embodiment. FIG. 4 is an enlarged perspective view showing a state where the reed is fixedly mounted according to the first embodiment. FIG. 5 is a wiring diagram showing a circuit portion according to the first embodiment. In the drawings, reference numeral 1 denotes a box-shaped base that houses therein e.g. a drive mechanism of the device according to the first embodiment. A rotating table 2 having discoidal shape is disposed on one side of the front surface of the base 1. That is, a rotation shaft 3 is vertically supported by the base 1, of which front end portion is projected from the surface of the base 1. The rotating table 2 is fixed around the portion of the rotation shaft 3 projecting from the surface of the base 1. A gear 4 is fixed on a portion of the rotation shaft 3 located inside of the base 1. The gear 4 is meshed with a gear 6 that is fixed on a rotating shaft of a rotary potentiometer 5 disposed inside of the base 1.

A fastening mechanism of the reed is provided on the surface of the rotating table 2. In the first embodiment, this fastening mechanism includes a holder 10 for mounting the reed therein, and a holder guiding member 11 fixed on the surface of the rotating table 2 for mounting the holder 10 therein. The holder guiding member 11 is a channel-shaped (groove-shaped) member fixed on the rotating table 2, of which longitudinal center line passes through the center of the rotation axis of the rotating table 2.

A scale board 2a having square shape is disposed to the side of the holder guiding member 11 close to center of the rotating table 2. This scale board 2a is provided for aligning a longitudinal position of the holder 10 (longitudinal position of the reed) that is mounted within the holder guiding member 11. That is, on the scale board 2a, described are a linear scale having a number of lines that are parallel to the central axis of the reed R and a semicircular scale having a plurality of semicircles (five semicircles in the illustrated example) that are coaxial with a center point of the rotating table 2. The linear scale is provided for aligning a longitudinal position of the reed fastened on the holder 10 such that the center line of the reed passes through the center point of the rotating table. The semicircular scale is provided for aligning an edge position of the reed R, and when the holder 10 is moved back and forth along the holder guiding member 11, the semicircular scale is served as a ruler for placing the reed R on the position where a trajectory of a probe 20 abutting the edge of the reed R draws an arc-shape upon rotating the rotating table 2.

The holder guiding member 11 is attached with fastening means 12 for fastening the holder 10 that is mounted within the holder guiding member 11. This fastening means 12 consists of a lever 12a having a substantially U-shape and a holding member 12b attached to the lever 12a. Respective ends of the U-shape of the lever 12a are pivotally supported on respective side surfaces of the holder guiding member 11. One end of the holding member 12b is pivotally attached to a center flat portion of the U-shape of the lever 12a, while the other end is served as a fastening portion of the holder 10.

The holder 10 is a channel-shaped member which is fitted within the holder guiding member 11 without any space. A holder bar 13 is fixed on a portion of the holder 10, which locates slightly closer to the rotation shaft 3 than the center portion of the holder 10, so that the holder bar 13 crosses over the channel. Space is formed between the holder bar 13 and the bottom surface of the channel of the holder 10 such that the test object reed as well as a wedge W for fixing the reed can be inserted into the space.

The probe 20 and its supporting member 21 are disposed on a portion of the base 1 located at the opposite side against the rotating table 2. That is, two rails 22a, 22b are disposed within an interior of the base 1 and extend in the longitudinal direction of the base 1 (toward the rotating table 2), and the supporting member 21 having a box-shape is slidably supported on the rails 22a, 22b. In order to move the supporting member 21, a rack 21a is provided on a bottom surface of the supporting member 21, and a pinion 23a meshes with the rack 21a. A support shaft of the pinion 23a is projected on the outer surface of the base 1, and a knob 23 is disposed on the projecting portion of the support shaft. Accordingly, the pinion 23a is rotated by rotating the knob 23 so that the supporting member 21 attached with the rack 21a is moved back and forth on the rails 22a, 22b.

The probe 20 comprises, for example, a needle portion 20b including a tip end equipped with a spherical portion 20a that serves for a contacting portion with the reed, a support tube 20c into which a base end portion of the needle portion 20b is inserted, and a plastic support plate 20d on which the support tube 20c is fixed. A displacement sensor 30 for detecting small displacement (angle variation) of the probe 20 as an electric signal is attached on the support plate 20d. A base end portion of the support plate 20d is fixed on the front surface of the box-shaped supporting member 21.

The outputs from the displacement sensor 30 are connected to a processing circuit 31. The processing circuit 31 is equipped with a characteristic graph creation unit 31a that creates a curve graph showing the variation in the displacement amount of the probe 20 is created for each rotation angle of the rotating table 2 detected by the rotary potentiometer 5. Furthermore, the processing circuit 31 comprises a characteristic graph storing unit 31b that stores the characteristic graph created by the creation unit 31a, and a comparative calculation unit 31c that makes comparative calculations of a plurality of stored characteristic graphs so as to obtain desired test results. The outputs from the processing circuit 31 are connected to a display unit 32 that displays a calculation result of the comparative calculation unit 31c by means of such as graphs and values.

The characteristic graph storing unit 31b stores various kinds of characteristic graphs created by the creation unit 31a, for example in accordance with the following classifications:
(1) a front-side characteristic graph of the test object reed;
(2) a back-side characteristic graph of the test object reed;
(3) a front-side characteristic graph of the reference reed; and
(4) a back-side characteristic graph of the reference reed.

The comparative calculation unit 31c makes the following calculations with respect to each of the characteristic graphs created by the creation unit 31a, and the results of such calculations are displayed on the display unit 32. Additionally, as a technique for display on the display unit 32, an area where the graphs overlap with each other may be discriminated by color, the area may be indicated by numerical values, or the area size may be indicated by gradual evaluations.

(a) Rigidity Distribution Characteristics of the Front and the Back Sides
The back-side characteristic graph of the test object reed is reversed left-to-right and displayed on the same screen as the front-side graph.
(b) Balance Index
Areas resultantly generated by overlapping the front-side characteristic graph of the test object reed with the reversed graph thereof is indicated as front-side balance index.
Areas generated by overlapping the back-side characteristic graph of the test object reed with the reversed graph thereof is indicated as back-side balance index.
The average value between the front-side balance index and the back-side balance index is indicated as total balance index of the front and back sides.
(c) Hardness Index
Ratio A1/S1, wherein A1 denotes an integral value of the front-side characteristic of the test object reed and S1 denotes an integral value of the front-side characteristic of the reference reed.
Ratio A2/S2, wherein A2 denotes an integral value of the back-side characteristic of the test object reed and S2 denotes an integral value of the back-side characteristic of the reference reed.
(A1/S1+A2/S2)/2 is indicated as the hardness of the test object reed.

(Operation of First Embodiment)
The following is an operation of the first embodiment having the above structure.
(1) Mounting of the Reed
In order to mount the test object reed R on the holder 10, a base end portion of the reed R is inserted between the bottom surface of the channel-shaped holder 10 and the holder bar 13, and fastened therein by inserting a wedge between the reed R and the bottom surface of the holder 10. In this case, the reed R is fastened to the holder 10 such that the vibrating tip of the reed R is projected from one end of the holder 10 that locates close to the center of the rotating table 2.

The projecting amount of the reed R from the holder 10 is determined such that when the holder 10 fastening the reed is mounted in the holder guiding member 11, the spherical portion 20a equipped on the tip end of the probe 20 becomes contact with the reed at the position about 1 mm inside from the edge of the vibrating tip of the reed R. Furthermore, the thickness of the bottom portion of the holder 10, the thickness of the wedge W, and the position of the holder bar 13 are determined such that the height from the surface of the rotating table 2 to the vibrating tip of the reed R becomes the same whether the holder 10 is facing upward or downward as shown in the upper portion of FIG. 3.

Next, the holder 10 fastening the reed R is faced upward and mounted within the holder guiding member 11. The scale board 2a is disposed to the side of the holder guiding member 11 close to the center of the rotation shaft. Therefore, with reference to the scale described on the scale board 2a, the holder 10 as a whole is moved back and forth within the holder guiding member 11 so as to align the position of the reed R. In this state, the end portion of the holding member 12b of the fastening means 12 attached to the holder guiding member 11 is applied on the upper surface of the holder 10, and then the lever 12a is raised vertically, thereby fastening the holder 10 on the guiding member 11.

In this state, the knob 23 is turned to move the supporting member 21 along the rails 22a, 22b so that the spherical portion 20a on the tip end of the probe 20 is made contact with the reed at the position about 1 mm inside from the edge of the vibrating tip of the reed R. In this case, the probe 20 is pressed against the surface of the reed R with the given pressing force because of the elasticity of the plastic support plate 20d that supports the needle portion 20b. Accordingly, the support plate 20d is deformed by the reacting force from the reed R, and the deformation degree of the support plate 20d is detected as an electric signal by means of the displacement sensor 30.

Figure 6A:
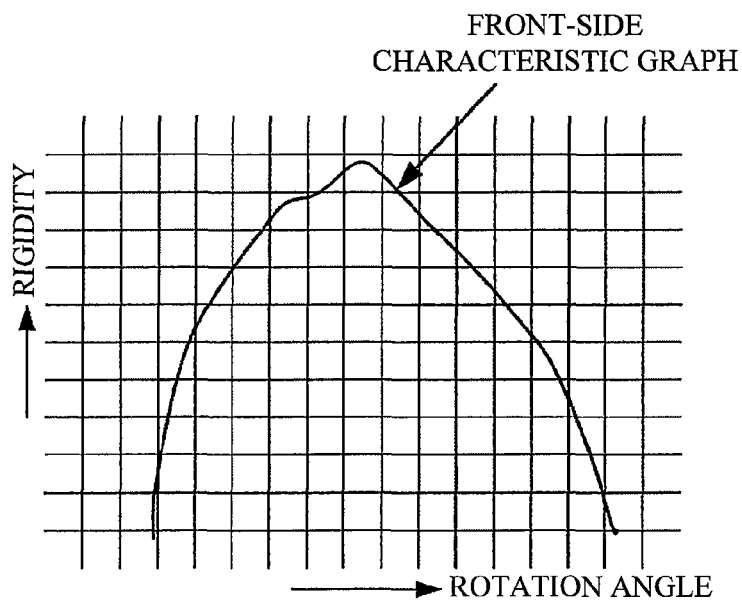
FIG. 6A-6D are waveform charts showing test results by means of the device according to the first embodiment and also showing means for obtaining an index for the right and left balance and an index for comparison to the reference reed.

In such state where the probe 20 is in elastically contact with the reed R, when the rotating table 2 is manually rotated, the output from the potentiometer 5 detecting the rotation angle of the rotating table 2 and the displacement amount of the probe 20 detected by the displacement sensor 30 are transmitted to the processing circuit 31. The graph creation unit 31a of the processing circuit 31 that has received these data creates the front-side characteristic graph of the reed R, as shown in FIG. 6A. This characteristic graph is stored in the graph storing unit 31b of the processing circuit 31.

Next, in order to inspect the back-side characteristic of the reed R, the fastening means 12 is removed, the holder 10 is removed from the guiding member 11 with the reed R remaining fastened to the holder, the holder 10 is turned upside down, again mounted on the guiding member 11, and fastened by the fastening means 12. The following process is similar to the above, that is, the rotating table 2 is rotated, and the back-side characteristic graph of the reed R is created and stored in the storing unit 31b. Furthermore, also with respect to the reference reed which is to be compared to the test object reed, the characteristics with respect to both the front and the back surfaces are measured, and the graphs thereof are stored in the storing unit 31b. By utilizing the respective stored characteristic graphs, the calculations necessary for indicating the characteristics of the reed R described in the above (a)-(c) are performed in the comparative calculation unit 31c.

(a) Rigidity Distribution Characteristics of the Front and the Back Sides

Figure 6B:
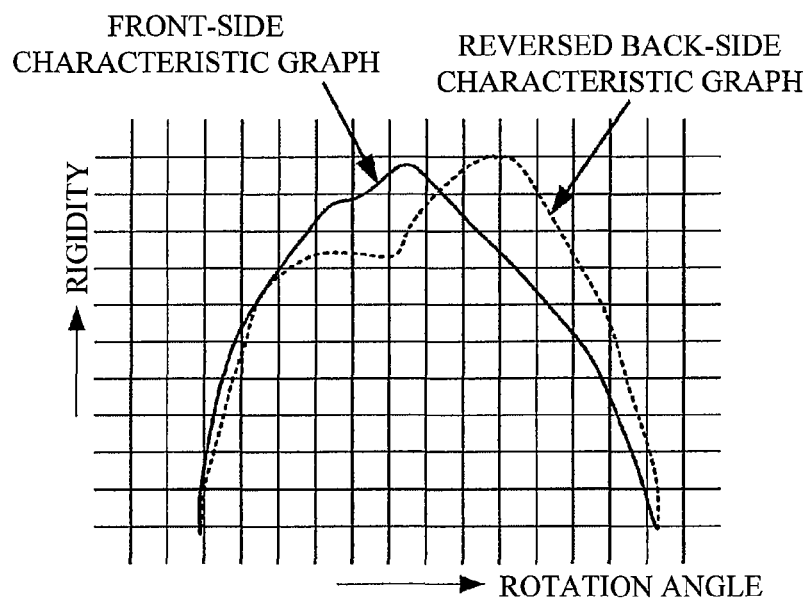

In the comparative calculation unit 31c, another characteristic graph is created by reversing left and right of the back-side characteristic graph of the test object reed obtained aforementionedly with respect to center line of the reed R. This reversed back-side characteristic graph is displayed on the same screen of the display unit 32 as the front-side characteristic graph stored in the storing unit 31b. FIG. 6B shows an example in which the front-side characteristic graph is displayed on the same screen as the reversed back-side graph by superimposing the graphs with each other. In this case, colors of the both graphs may be different with each other, or the both graphs may be displayed by arranging the graphs vertically to each other. Those have an advantage that it becomes easier to identify the position of the vascular bundle that causes the performance deterioration of the reed R.

(b) Balance Index

Figure 6C:
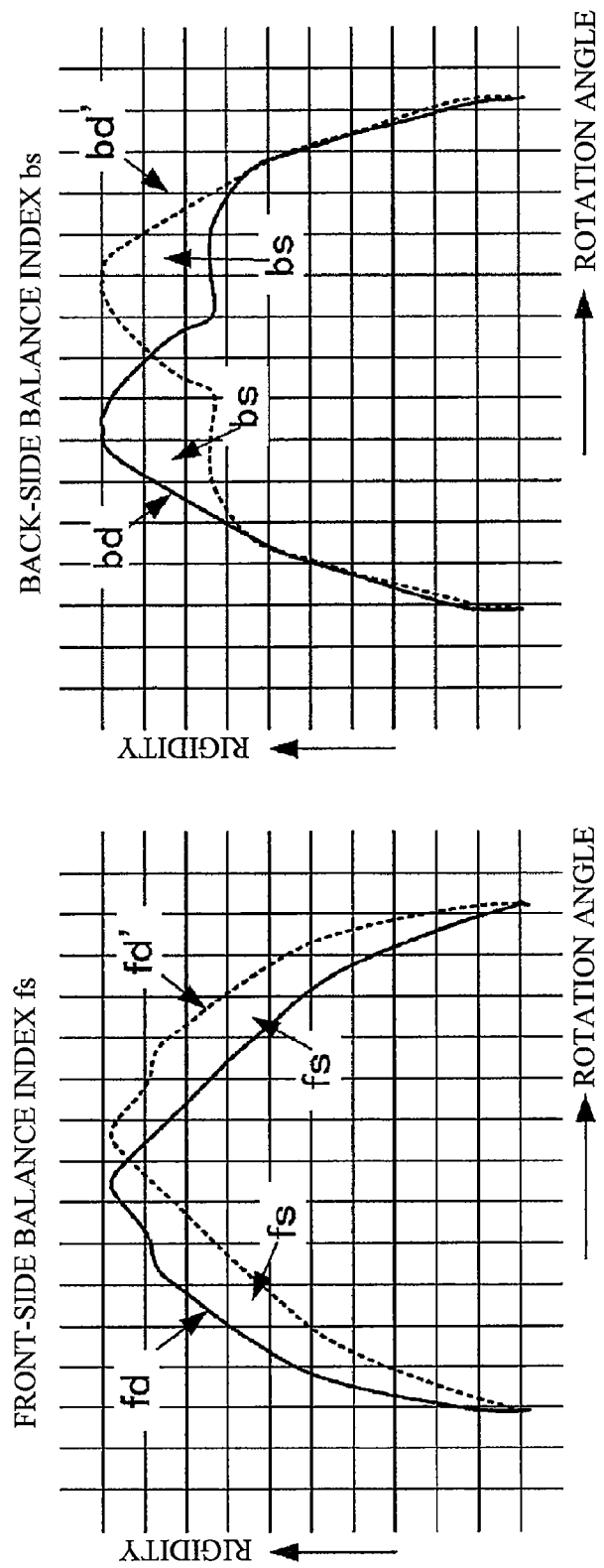

As shown in FIG. 6C, in the comparative calculation unit 31c, the front-side characteristic graph fd of the test object reed is superimposed with the graph fd' that is created by reversing left and right of the graph fd, and the resultantly generated area fs is indicated as front-side balance index. Similarly, the back-side characteristic graph bd is superimposed with the graph bd' that is created by reversing left and right of the graph bd, and the resultantly generated area bs is indicated as back-side balance index. Thus obtained average value between the front-side balance index fs and the back-side balance index bs, that is, (fs+fb)/2 is indicated as total balance index of the front and the back sides. This balance index is useful as an objective index of the reed, and this testing data can be used as a warranty of the performance of the reed by attaching the data on the selling reed.

(c) Hardness Index

Figure 6D:
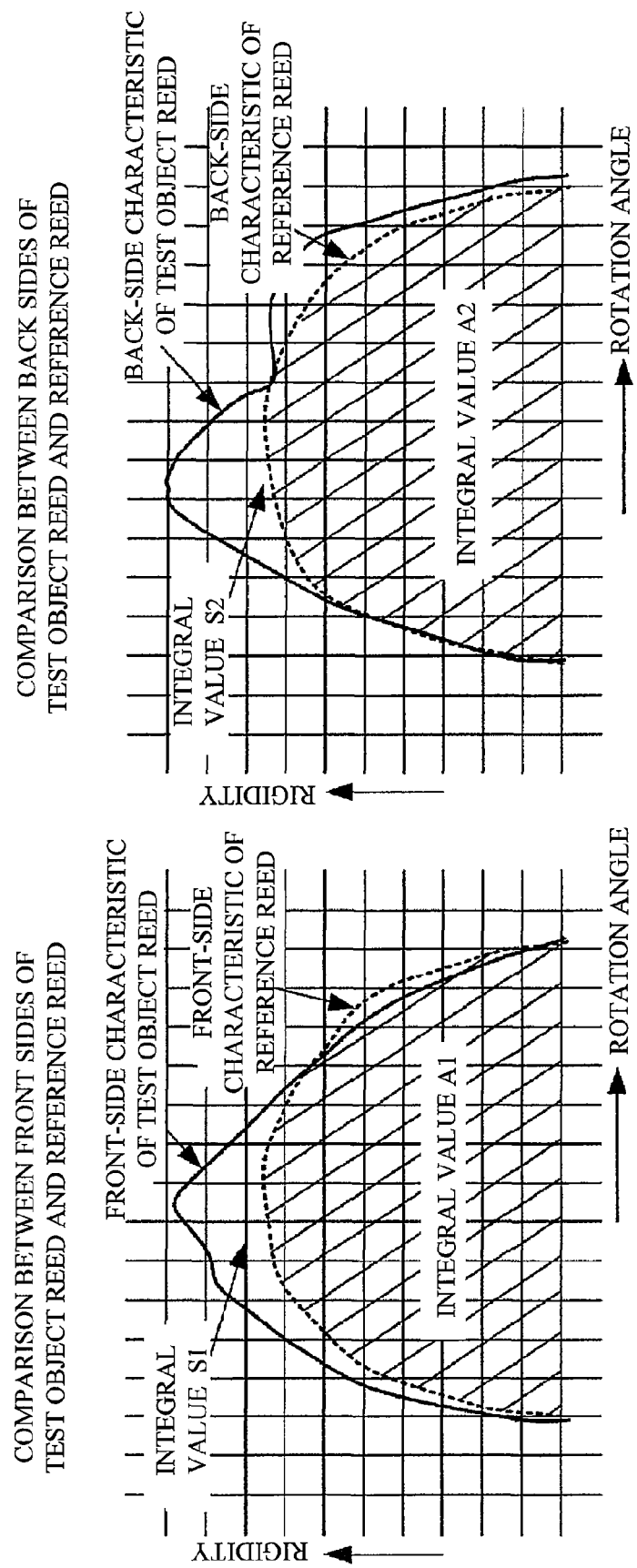

As shown in FIG. 6D, in the comparative calculation unit 31c, calculations are made with respect to the ratio A1/S1, where A1 denotes an integral value of the front-side characteristic of the test object reed, and S1 denotes an integral value of the front-side characteristic of the reference reed, as well as the ratio A2/S2, where A2 denotes an integral value of the back-side characteristic of the test object reed, and S2 denotes an integral value of the back-side characteristic of the reference reed, and the average value (A1/S1+A2/S2)/2 between thus obtained values is indicated as the hardness of the test object reed.

Under the present circumstances, the hardness of the reed is indicated by different indices of respective manufacturers, therefore, between the different manufacturers, the hardness of the reeds cannot be compared with reference to the common standard. Furthermore, even if the reeds are manufactured by the same manufacturer and indicated that the hardness is "3", those may include a reed which should be actually classified to "2" or "4". There provides a table of compatibility for comparing the hardness between the reeds manufactured by different manufacturers, though, this table only gives a rough standard. In contrast, according to the first embodiment, objective indication of the hardness without variation can be achieved and the testing data can be used as a warranty of the performance of the reed by attaching the data on the selling reed. Furthermore, by storing the characteristic data of the reference reed, rigidity changing of the test object reed due to aging also can be traced.

(Second Embodiment)

Figure 7:
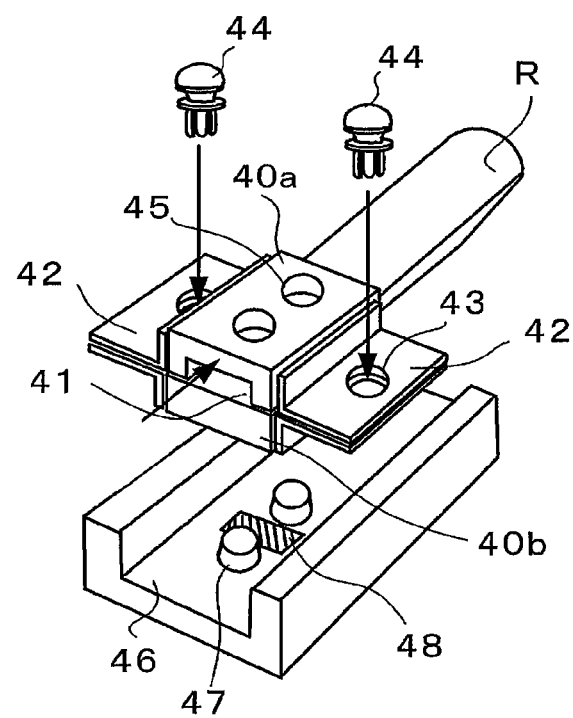
FIG. 7 is an enlarged perspective view showing a mounting portion of the reed according to a second embodiment.

FIG. 7 is an enlarged perspective view showing a mounting portion of the reed R according to a second embodiment of the present invention. The second embodiment employs means for turning the reed R upside down to be mounted on the rotating table 2, in which the base end portion of the reed R is held between two-divided upper and bottom holders 40a, 40b. In an example shown in FIG. 7, a recess 41 is provided on the upper holder 40a, into which the base portion of the reed R is inserted, and the reed R mounted on the recess 41 is held between the upper and the bottom holders. Flanges 42 are fixed on respective side surfaces of the upper and the bottom holders 40a, 40b by means of screwing, welding, adhering, etc. In a state where the flanges 42 of the upper and the bottom holders are overlapped with each other, clips 44 prepared separately are inserted into holes 43 formed on the flanges 42 thereby fastening the upper and the bottom holders.

A pair of positioning holes 45, 45 are respectively formed on the top surface of the upper holder 40a and the bottom surface of the bottom holder 40b, and pins 47, 47 disposed on a bottom portion of a holder guiding member 46 are respectively fitted into the respective positioning holes 45, 45, thereby aligning the positions of the upper and the bottom holders holding the reed R therebetween. In this case, by disposing a magnet 48 under a bottom surface of the holder guiding member 46 and constituting the holders 40a, 40b by a metal attracted to the magnet, e.g. iron, it becomes unnecessary to provide metal fittings for fastening the holders 40a, 40b on the holder guiding member 46.

These holders make it possible to turn the reed R upside down and mount the reed on the rotating table 2 by easier structure than using the holder according to the first embodiment. Furthermore, operations such as positioning the holders on the holder guiding member, turning the holders upside down and mounting the holders on the holder guiding member also become easier. In this embodiment, the holders and the holder guiding member are fastened on a fixed position, however, longitudinal position of the reed R can be aligned by sliding the reed R back and forth within the recess 41 of the holder 40a.

(Third Embodiment)

Figure 8:
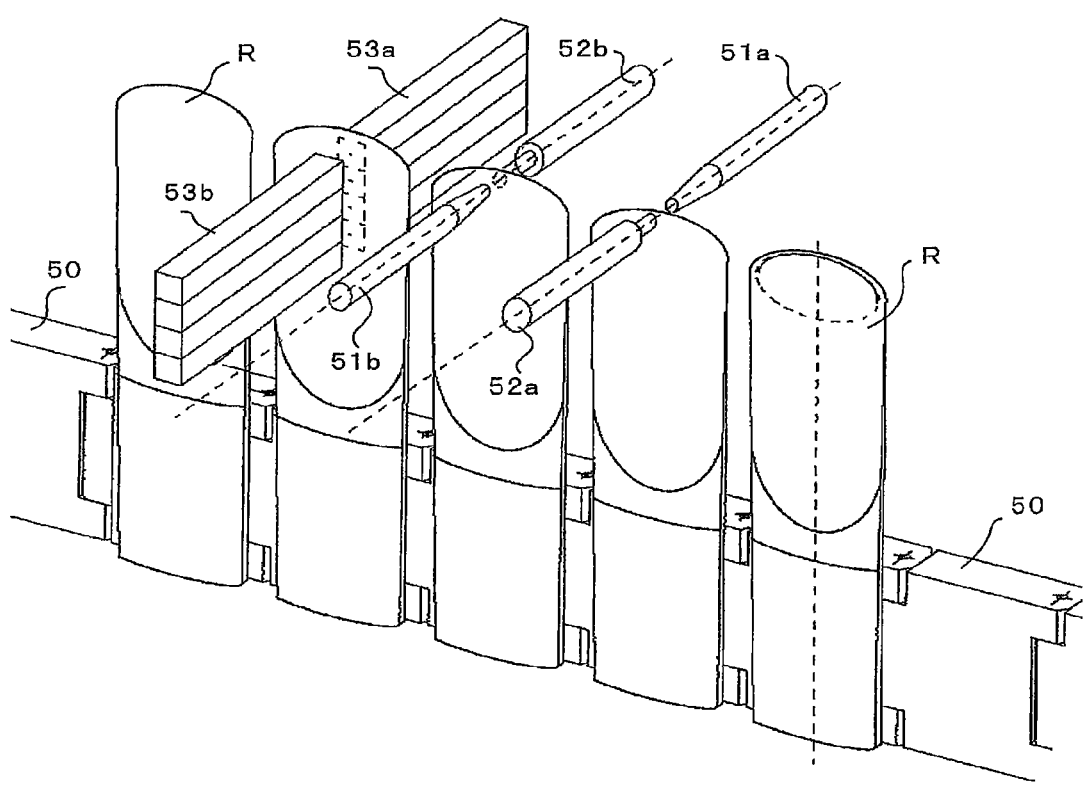
FIG. 8 is an enlarged perspective view showing a mechanism portion according to a third embodiment.

FIG. 8 is a perspective view showing a third embodiment of the present invention. The third embodiment is directed to a device suitable for continuously testing a large number of reeds. In the third embodiment, the reeds R are continuously transferred by a chain conveyor 50. The fastening means between the reeds R and the chain conveyor 50 is not illustrated in FIG. 8, though, it is possible that the base end portion of the reed is inserted into a pocket attached on the side surface of the conveyor, or the base end portion of the reed is fastened by a clip provided on the conveyor.

Air nozzles 51a, 51b are used as means for displacing the reeds R and apply local pressure on the front and the back surfaces of the reeds. In this case, it is preferable that the air is set to a condition that the temperature is 37° C. and the humidity is 100%. Furthermore, it is preferable that the reeds are soaked into tepid water of 37° C. for about 3 minutes before measuring the reed. For this purpose, a hot water tank may be provided on a path of the chain conveyor 50, and the reeds mounted on the chain conveyor are passed through the hot water tank thereby continuously warming and humidifying the reeds. Other than the air, nitrogen also can be used as a gas for applying pressure on the reeds.

Optical non-contact type displacement sensor measuring devices 52a, 52b are provided as opposed to the air nozzles 51a, 51b respectively for the front and the back sides of the reed R, with placing the reed R therebetween. The optical non-contact type sensor displacement measuring devices 52a, 52b do not directly contact with the reed, thereby having an advantage that any friction causing damage to the reed and the probe is not generated. As the non-contact type sensor displacement measuring device, a laser beam triangulation system and an optical fiber type measurement system are applicable.

The scanning trajectory of the rigidity measurement point may be linear along the traveling direction of the chain conveyor, though, it is preferable that the trajectory has an elliptic shape of which oblateness is about 50% and located 1 mm inside from the edge of the reed, as illustrated by the dotted line in the reed R of FIG. 8. This is because that the elliptic shape is close to the shape of the edge portion of the general reed, and further by scanning the reed from both the right and left of the width direction thereof, the hysteresis error can be eliminated.

In the third embodiment, a characteristic graph showing the rigidity distribution of the reed is created based on the outputs from the non-contact type displacement measuring devices 52a, 52b and movement trajectory data of the air nozzles, and the aforementioned (a)-(c) are indicated as similar to the first embodiment. Furthermore, in the third embodiment, subsequent to the air nozzles 51a, 51b and the non-contact type displacement measuring devices 52a, 52b provided for detecting the rigidity, is provided means for correcting the rigidity distribution characteristics by cutting the vascular bundle of the reed based on the test result. FIG. 8 shows laser diodes 53a, 53b as means for cutting the vascular bundle.

With reference to the characteristic graphs obtained by the test means, if the rigidity of the reed exceeds a predetermined allowable value, or the right and left balance is not suitable, the laser diodes 53a, 53b cut the vascular bundle having high rigidity and thus causing such defect. Accordingly, the comparative calculation unit 31c of the first embodiment detects a portion having a higher rigidity than the other portions in the characteristic graphs from e.g. the following criteria:

(1) a portion having larger inclination of the graph compared to the other portions; and (2) upon superimposing the characteristic graph with the reversed graph thereof, a portion where difference between the values of the both graphs exceeds the given value, and cut the vascular bundle corresponding to such portion by the laser diodes 53a, 53b.

The laser diodes 53a, 53b can cut the vascular bundle without contacting to the reed and applying unnecessary pressure to the reed, therefore there is no risk of performance deterioration of the reed. Moreover, cutting performance of the laser diode is not deteriorated since it does not contact to the reed, therefore it is suitable to cut the minute portion, i.e. the vascular bundle. The cutting depth of the vascular bundle ranges from 0.1 mm and does not exceed 0.5 mm even in the large-type reed, therefore it is possible to use the low-power laser diode.

For the purpose of correcting the rigidity distribution characteristics, in addition to the laser diode, a minimal knife also can be used as the cutting means of the vascular bundle. In this case, the vascular bundle can be cut more smoothly by vibrating the knife ultrasonically.

According to the third embodiment configured as above, characteristics of a large number of the reeds can be tested continuously. Furthermore, regarding the test result, it becomes possible to not only indicate the result but also sound an alarm against the reed of which index is out of the suitable value, or automatically sort such reed from the chain conveyor as a defective product or a product necessary to be repaired. Moreover, according to the third embodiment, the vascular bundle is cut by using the laser diode with reference to the test result, therefore the rigidity distribution characteristics can be automatically corrected to the suitable value. As a result, by supplying reeds shaped by cutting into the device according to the third embodiment, it becomes possible to manufacture reeds having properly controlled rigidity distribution characteristics.

(Fourth Embodiment)

The present invention is not limited to the above described embodiments, but also includes the following embodiments.

(1) In the first embodiment, a box-shaped member is used as a member for supporting the probe 20, however, it is not necessary to be limited to this type. That is, a supporting member is attached to a box-shaped member as movable up and down or as rotatable, and the probe 20 can be supported by this supporting member. In this case, when the reed is mounted on the rotating table 2, replacement of the reed can be performed easily without contacting the reed with the tip end of the probe 20 by raising the tip end of the probe 20 upwardly. Furthermore, after the measurement is finished, the tip end of the probe 20 is released from the surface of the reed, therefore the extra load is not added to the reed and thus the deformation or characteristic change of the test object reed will not occur.

(2) In the present invention, various means can be used for turnably mounting the reed on the rotating table. In addition to the mechanisms described in the first embodiment and the second embodiment, it is also possible to use mechanisms in which the holder holding the reed therein is turned hinge-like with respect to the support shaft, or the holder is automatically turned by using e.g. a motor. Furthermore, it is also possible to enlarge the range of automation from the supply of the reed to the mounting of the reed on the holder, and turning of the holder.

Figure 9:
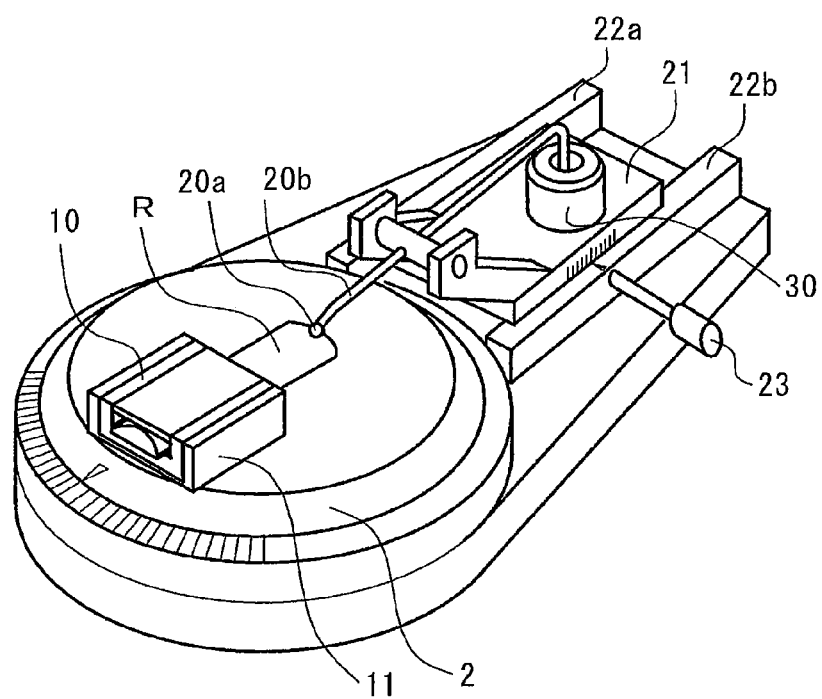
FIG. 9 is an enlarged perspective view showing a mounting portion of the reed according to a fourth embodiment.

(3) As shown in FIG. 9, the present invention can also be realized by providing the holder guiding member 11 and the holder 10 on the reed testing device disclosed in Patent document 1.

The invention claimed is:

1. A reed testing device for a single-reed instrument comprising:
   a displacement sensor which detects rigidity distribution characteristics of a reed in a width direction thereof with respect to both a front and a back surfaces of the reed;
   a characteristic graph creation unit which creates characteristic graphs showing variation in the rigidity distribution characteristics of the reed with respect to the front and the back surfaces of the reed based on outputs from said displacement sensor;
   a characteristic graph storing unit which stores the characteristic graphs of the front and the back surfaces created by said characteristic graph creation unit;
   a comparative calculation unit which creates a graph by reversing left and right of the characteristic graph of the back surface of the reed created by said characteristic graph creation unit with respect to a longitudinal center line of the reed; and
   a display unit which displays the characteristic graph of the front surface created by said characteristic graph creation unit and the reversed characteristic graph of the back surface of the reed created in said comparative calculation unit on one screen, wherein:
      said comparative calculation unit superimposes the characteristic graphs obtained with respect to the front and the back surfaces of the reed with the graphs obtained by reversing left and right of said characteristic graphs, quantitatively determines differences between the created characteristic graphs and the reversed characteristic graphs, and outputs an index regarding a right and left balance of the reed.

2. The reed testing device for the single-reed instrument according to claim 1, wherein:
   said comparative calculation unit compares characteristics of a reference reed with characteristics of a test object reed, and a comparison result is displayed quantitatively.

3. The reed testing device for the single-reed instrument according to claim 1, further comprising:
   a holder which holds a base end portion of the reed in a state enabling free displacement of a vibrating tip of the reed and a holder guiding member on which said holder is mounted, wherein:
      the holder which holds the reed therein is turnably mounted on the holder guiding member such that the front surface or the back surfaces of the reed faces upwardly.

4. The reed testing device for a single-reed instrument according to claim 1, further comprising a pressure-applying device applying a pressure force on the reed, wherein
   the displacement sensor detects rigidity distribution characteristics of the reed by detecting displacement of the reed caused by the pressure force from the pressure applying device or by detecting displacement of the pressure-applying device caused by a reacting force from the reed upon applying the pressure force on the reed.

5. The reed testing device for a single-reed instrument according to claim 1, further comprising a probe which applies a pressure force on the reed, wherein
   the displacement sensor detects rigidity distribution characteristics of the reed by detecting displacement of the probe caused by a reacting force from the reed upon applying the pressure force on the reed.

6. A reed testing device for a single-reed instrument comprising:
   a displacement sensor which detects rigidity distribution characteristics of a reed in a width direction thereof with respect to both a front and a back surface of the reed;
   a characteristic graph creation unit which creates characteristic graphs showing variation in the rigidity distribution characteristics of the reed with respect to the front and the back surfaces of the reed based on outputs from said displacement sensor; and
   a nozzle for blowing pressurized gas on the reed, wherein:
      said displacement sensor obtains the rigidity distribution characteristics of the reed by detecting a displacement of the reed caused by the pressurized gas from the nozzle.

7. The reed testing device for the single-reed instrument according to claim 6, further comprising a conveyor for continuously conveying a plurality of reeds, wherein the nozzle and the displacement sensor are arranged to be faced towards each other with a traveling path of the conveyor positioned therebetween.

8. The reed testing device for the single-reed instrument according to claim 7, wherein:
   a cutting member is arranged subsequent to the displacement sensor for cutting a vascular bundle of the reed based on a shape of an obtained characteristic graph.

9. A method for testing a reed for a single-reed instrument comprising:
   a first step of detecting rigidity distribution characteristics of a front surface of the reed in a width direction thereof by means of a displacement sensor;
   a second step of detecting rigidity distribution characteristics of a back surface of the reed in the width direction thereof by means of the displacement sensor;
   a third step of creating characteristic graphs showing variation in the rigidity distribution characteristics of the front and the back surfaces of the reed by using the rigidity distribution characteristics detected in the first and second steps respectively by means of a characteristic graph creation unit;
   a fourth step of storing the characteristic graph of the front surface created in the third step by means of a characteristic graph storing unit;
   a fifth step of storing the characteristic graph of the back surface created in the third step by means of the characteristic graph storing unit;
   a sixth step of creating a reversed characteristic graph by reversing left and right of the characteristic graph of the back surface of the reed created in the third step with respect to a longitudinal center line of the reed by means of a calculation unit;
   a seventh step of displaying the characteristic graph stored in the fourth step together with the reversed characteristic graph created in the sixth step on one screen by means of a display unit; and
   an eighth step of superimposing the characteristic graphs obtained with respect to the front and the back surfaces of the reed with the graphs obtained by reversing left and right of said characteristic graphs, quantitatively determining differences between the created characteristic graphs and the reversed characteristic graphs and outputting an index regarding a right and left balance of the reed.

* * * * *